United States Patent
Dejneka et al.

(10) Patent No.: US 7,919,328 B2
(45) Date of Patent: Apr. 5, 2011

(54) FLUORESCENT ION DOPED GLASS AND METHOD FOR USING THE FLUORESCENT ION DOPED GLASS TO ENHANCE FLUORESCENCE IMAGING TECHNIQUES

(75) Inventors: Matthew J. Dejneka, Corning, NY (US); Hui Su, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 1043 days.

(21) Appl. No.: 11/715,005

(22) Filed: Mar. 7, 2007

(65) Prior Publication Data
US 2007/0212793 A1    Sep. 13, 2007

Related U.S. Application Data

(60) Provisional application No. 60/781,567, filed on Mar. 10, 2006.

(51) Int. Cl.
*G01N 21/76* (2006.01)
*G01N 33/20* (2006.01)
(52) U.S. Cl. .......................... 436/172; 436/82
(58) Field of Classification Search .................. 436/172, 436/82
See application file for complete search history.

(56) References Cited

U.S. PATENT DOCUMENTS

| | | | |
|---|---|---|---|
| 6,648,506 B2 * | 11/2003 | McGrath et al. | 374/161 |
| 2003/0048437 A1 * | 3/2003 | Kalal et al. | 356/128 |
| 2004/0043502 A1 * | 3/2004 | Song et al. | 436/172 |
| 2005/0017191 A1 | 1/2005 | Montagu et al. | 250/393 |

FOREIGN PATENT DOCUMENTS

WO    WO 2005/000760    1/2005

OTHER PUBLICATIONS

M.J. Dejneka et al., "Rare Earth-Doped Glass Microbarcodes", PNAS, Jan. 21, 2003, vol. 100, No. 2, pp. 389-393.
"Top-Hat Beam Shaping—Circular and Rectangular Top-Hat Beam Shaper", http://www.holoor.co.il/website/data/products/top_hat_beam/top%20hat%20shaper1.htm, pp. 1-2.
GenePix® Pro 5.0, "Microarray Acquisition and Analysis Software for Genepix Microarray Scanners", Software Manual, pp. 1-100.

* cited by examiner

*Primary Examiner* — Lore Jarrett
(74) *Attorney, Agent, or Firm* — John L. Haack

(57) ABSTRACT

A fluorescent ion doped glass (or other fluorescing material) and a method for using the fluorescent ion doped glass to enhance a fluorescence imaging technique are described herein. In one embodiment, the fluorescent ion doped glass (or other fluorescing material) is used as a calibration standard to check the uniformity of an intensity profile of an excitation source. In another embodiment, the fluorescent ion doped glass (or other fluorescing material) is used as an offline calibration standard to normalize a native fluorescence image of one or more test samples (e.g., a protein array). In yet another embodiment, the fluorescent ion doped glass (or other fluorescing material) is used as an online calibration standard to normalize a native fluorescence image of one or more test samples (e.g., a protein array).

13 Claims, 10 Drawing Sheets

FLUORESCENT ION DOPED GLASS AND METHOD FOR USING THE FLUORESCENT ION DOPED GLASS TO ENHANCE FLUORESCENCE IMAGING TECHNIQUES

CLAIMING BENEFIT OF PRIOR FILED U.S. APPLICATION

This application claims the benefit of U.S. Provisional Application Ser. No. 60/781,567 filed on Mar. 10, 2006. The contents of this document are hereby incorporated by reference herein.

TECHNICAL FIELD

The present invention relates to a fluorescent ion doped glass (or other fluorescing material) and a method for using the fluorescent ion doped glass (or other fluorescing material) as a reference standard to help enhance fluorescence imaging techniques (e.g., laser-based fluorescence imaging techniques, lamp-based fluorescence imaging techniques).

BACKGROUND

Referring to FIG. 1 (PRIOR ART), there is a block diagram illustrating the basic components of an exemplary fluorescence array imager 100 which is widely used today in the fields of chemistry, biochemistry and molecular biology. The exemplary fluorescence array imager 100 shown includes an excitation source 102 (e.g., laser, lamp, light emitting diode) which emits an optical beam 104 that is reflected by a dichroic mirror 106 and passed through a lens 108 before it illuminates a test sample 110 (which contains fluorescently labeled materials). In this example, the test sample 110 is a protein array 110 that is located within a well of a microplate 112.

The fluorescence array imager 100 also includes an imaging device 114 (e.g., charge-coupled device (CCD), photomultiplier tube (PMT)) which captures (receives) the fluorescence 105 that is emitted from the protein array 110. More specifically, the imaging device 114 captures the emitted fluorescence 105 after it passes through the lens 108, the dichroic mirror 106 and a filter 116. Then, the imaging device 114 creates and outputs a two-dimensional (2D) fluorescence image of the protein array 110. This is all possible, because when photons of a certain wavelength are emitted from the excitation source 102 and absorbed by certain molecules in the protein array 110, then those molecules emit fluorescence 105 at another wavelength. And, this emitted fluorescence 105 is what is captured by the imaging device 114.

In particular, the fluorescence array imager 100 implements one of two methods to create the 2D fluorescence image: (1) a narrow beam of light 104 (emitted from a laser 102) can be scanned across a region of interest on the protein array 110 and the emitted fluorescence 105 from each scanned location is collected by the PMT 114 and then later digitally composed into the 2D fluorescence image; or (2) a wide beam of light 104 (emitted from a lamp 102) can be used to illuminate the whole region of interest on the protein array 110 and the emitted fluorescence 105 from this region is collected by the CCD 114 (or a 2D photo detector 114) and directly composed into the 2D fluorescence image. In either case, the resulting 2D fluorescence image represents the intensity of the fluorescence 105 emitted from the molecules within the protein array 110.

A principle assumption in fluorescence imaging when a quantitative analysis is used to determine the concentration of molecules within a protein array 110 is that the intensity of the excitation source 102 is locally uniform, and the collection optics 106, 108 and 116 and imaging device 114 are uniform, and therefore the intensity of the emitted fluorescence 105 is going to have a linear relationship to the concentration of the molecules of interest. In view of this assumption, it follows that the intensity of the emitted fluorescence within the 2D fluorescence image can with a simple calibration be directly converted to indicate the concentration of the molecules of interest. Unfortunately, the assumption that the intensity of the excitation source 102 is locally uniform is not necessarily a correct assumption.

In PMT-based scanning fluorescence imaging techniques, the most commonly used excitation light source 102 is a laser because it can be focused to a very small optical beam 104 which then scans the region of interest on the protein array 110. The excitation energy of the scanned region of interest is going to be uniform if the laser's output intensity is stable in the time while the protein array 100 is scanned. However, the laser's output intensity often fluctuates and decays as a function of time which can cause artificial errors to be introduced into the 2D fluorescence image. This is not desirable.

In CCD-based fluorescence imaging techniques, the most commonly used excitation light source 102 is a lamp because it can better illuminate a sizable region of the protein array 110 when compared to a laser. However, the intensity of the lamp 102 is not always uniform which can cause artificial errors to be introduced into the 2D fluorescence image. In addition, the CCD 114 and collection optics may not be perfectly uniform because of: (1) the aging of the CCD 114; and (2) the accumulation of dust and dirt over time on the CCD 114 and collection optics. This is not desirable.

Lasers have also been used as an illumination source in CCD-based fluorescence imaging, however, the Gaussian distribution of a laser beam does not allow a quantitative measurement without a calibration of the laser's intensity. In the past, top-hat optics has been used in an attempt to help generate a relative uniform distribution of laser intensity. However, the use of top-hat optics sacrifices the total intensity output of the laser which would then limit the sensitivity of the measurement. This is not desirable.

Accordingly, there has been a need to address these shortcomings so one can use a fluorescence array imager 100 to obtain an "accurate" 2D fluorescence image of a protein array 110 (or other analyte array 110). In particular, there has been a need to obtain an "accurate" 2D fluorescence image which represents the concentration of the molecules of interest within the protein array 110 (or other analyte array 110) without being adversely affected by a non-uniform excitation source 102. This need and other needs are addressed by the present invention.

SUMMARY

A fluorescent ion doped glass (or other fluorescing material) and a method for using the fluorescent ion doped glass to enhance a fluorescence imaging technique are described herein. In one embodiment, the fluorescent ion doped glass is used as a calibration standard to check the uniformity of an intensity profile of an excitation source. In another embodiment, the fluorescent ion doped glass is used as an offline calibration standard to normalize a native fluorescence image of one or more test samples (e.g., a protein array). In yet another embodiment, the fluorescent ion doped glass is used as an online calibration standard to normalize a native fluorescence image of one or more test samples (e.g., a protein array).

BRIEF DESCRIPTION OF THE DRAWINGS

A more complete understanding of the present invention may be had by reference to the following detailed description when taken in conjunction with the accompanying drawings wherein.

DETAILED DESCRIPTION

Figure 1:
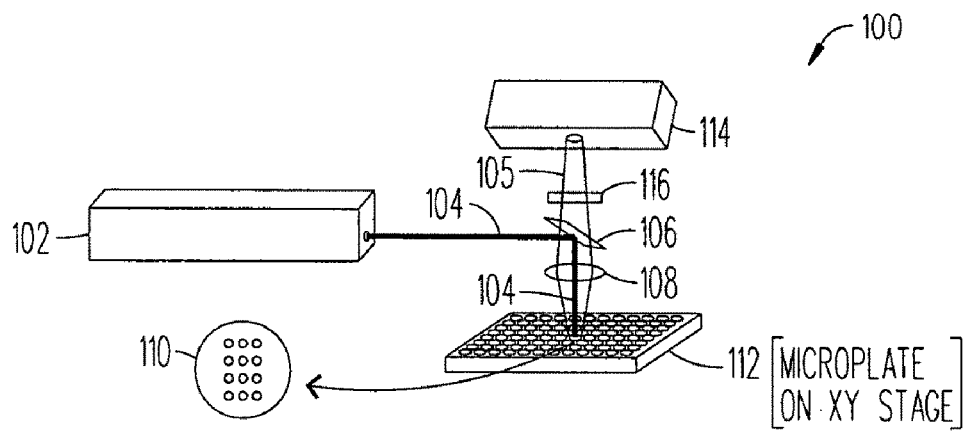
FIG. 1 (PRIOR ART) is a block diagram of an exemplary fluorescence array imager which is used to help explain some of the problems associated with traditional fluorescence imaging techniques.
Figure 2A:
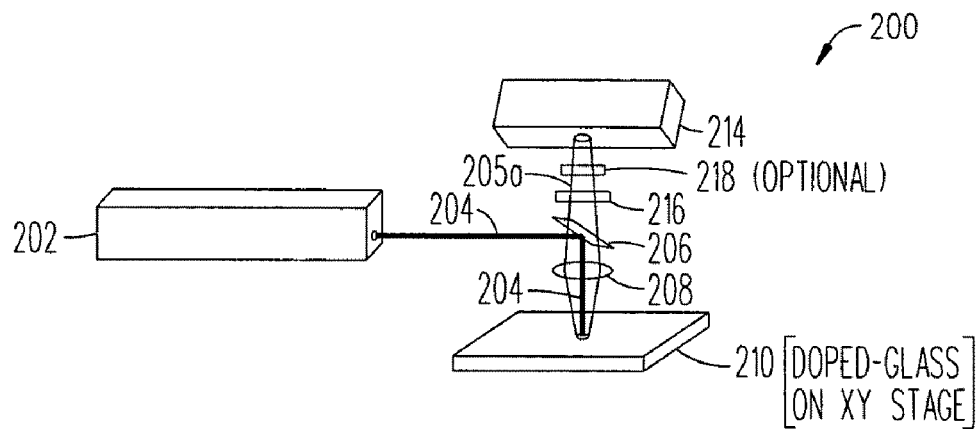
FIGS. 2A and 2B are two block diagrams of an exemplary fluorescence array imager which are used to help explain how a 2D fluorescent image of a fluorescent ion doped glass can be used to solve the aforementioned problems which are associated with traditional fluorescence imaging techniques in accordance with several different embodiments of the present invention.

Referring to FIG. 2A, there is a block diagram illustrating an exemplary fluorescence array imager 200 that is interrogating a fluorescent ion doped glass 201 to obtain a 2D fluorescent image which can be used as a calibration/reference to enhance a fluorescence imaging technique in accordance with several different embodiments of the present invention. The exemplary fluorescence array imager 200 shown includes an excitation source 202 (e.g., laser, lamp, light emitting diode) which emits an optical beam 204 that is reflected by a dichroic mirror 206 and passed through a lens 208 before it illuminates a piece of glass 201 which is homogeneously doped with a fluorescent ion. The fluorescent ion doped glass 201 absorbs light at the wavelength of the excitation source 202 and emits fluorescence 205a at another wavelength which is captured by an imaging device 214 (e.g., CCD, PMT, complementary metal oxide semiconductor (CMOS) camera) (see FIGS. 4 and 7). In one embodiment, the fluorescent ion doped glass 201 is homogeneously doped with rare earth ions like, for example, $Eu^{3+}$, $Sm^{3+}$, $Pr^{3+}$, $Gd^{3+}$, $Nd^{3+}$, $Yb^{3+}$, $Er^{3+}$, $Tm^{3+}$ and/or $Tb^{3+}$. Alternatively, the fluorescent ion doped glass 201 can be homogeneously doped with fluorescent ions like, for example, $Sn^{2+}$, $Mn^{n+}$, $As^{3+}$, $Pb^{2+}$, $Cu^+$, $Bi^{n+}$ and/or $Sb^{3+}$.

As shown, the imaging device 214 (e.g., CCD, PMT, CMOS camera) captures (receives) the fluorescence 205a which is emitted from the fluorescent ion doped glass 201. More specifically, the imaging device 214 captures the emitted fluorescence 205a after it passes through the lens 208, the dichroic mirror 206 and a filter 216. Then, the imaging device 214 outputs a 2D fluorescence image of the fluorescent ion doped glass 201. Because, the concentration of the fluorescent ions is a constant within the doped glass 201, the intensity of the fluorescence 205a emitted from the fluorescent ion doped glass 201 has a linear relationship to the intensity of the excitation source 202. As such, the 2D fluorescence image of the fluorescent ion doped glass 201 can serve as a profile of the intensity distribution of the excitation source 202, and it can be used as a reference/standard to (for example): (1) normalize a fluorescence image of a test sample (e.g., protein array); (2) check the uniformity of a laser light source which scans across the scanning area in a PMT based quantitative fluorescence imaging technique, and calibrate the fluorescence image if the intensity profile across the scanning region is repeatable; (3) check the uniformity of a lamp light source in a CCD-based fluorescence imaging technique, and calibrate the fluorescence image if the light intensity pattern is repeatable; and (4) correct the non-uniformities in the collection optics and detection system.

Figure 2B:
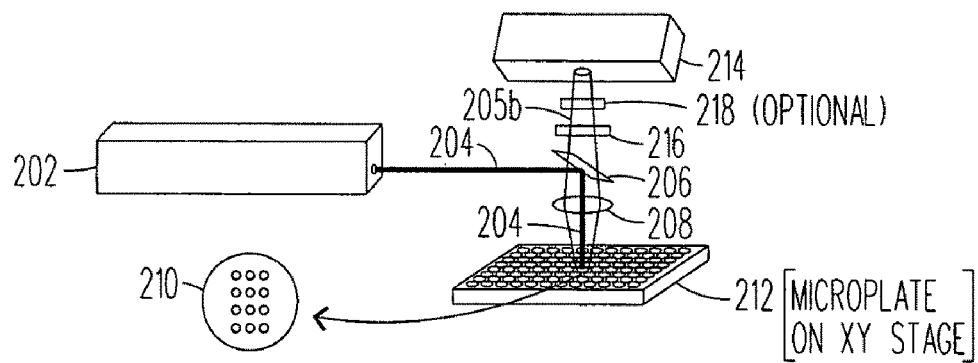

A detailed discussion is provided next about how the 2D fluorescence image of the fluorescent ion doped glass 201 can be used as a reference/standard to normalize the fluorescence image of a test sample. As shown in FIG. 2B, the fluorescence array imager 200 obtains the test sample's fluorescence image by interrogating the test sample which in this case is a protein array 210 that is located within the well of a microplate 212. Theoretically, the fluorescence intensity of each location (x, y), TargetFluorescenceIntensity (x,y), on the test sample's fluorescence image is a function of the concentration of fluorescing molecules, FluoroConcentration (x,y), and the power of the excitation source 202, SourceIntensity (x,y), at that specific location. This particular relationship can be represented as follows in equation no. 1:

TargetFluorIntensity(x,y)∝FluoroConcentration(x,y)
*SourceIntensity(x,y)

In the fluorescent ion doped glass 201, the concentration of fluorescing materials, ReferenceFluorescenceIntensity (x,y), is a constant, and therefore it's intensity can be represented as follows in equation no. 2:

ReferenceFluorintensity(x,y)∝SourceIntensity(x,y)

The fluorescence image of the fluorescent ion doped glass 201 could be considered as being an indirect profile of the photon density of the excitation source 202. Thus, the normalization of excitation source 202 can be performed by dividing the fluorescence the image of the fluorescent ion doped glass 201 from fluorescence image of the test sample as shown in equation no. 3:

NormalizedFluorescenceIntensity(x,y)=TargetFluorescenceIntensity(x,y)/ReferenceFluorescenceIntensity(x,y)~∝FluoroConcentration(x,y)*SourceIntensity(x,y)/SourceIntensity(x,y)
∝FluoroConcentration(x,y)

Figure 3:
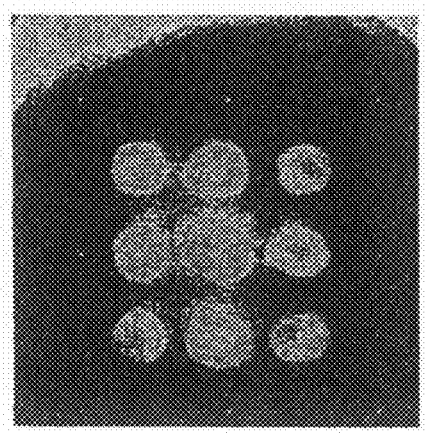
FIG. 3 is a raw (native) fluorescence image of a 3×3 NTR1 membrane protein array that was excited by a 355 nm laser which was associated with a fluorescence array imager that was set-up like the one shown in FIG. 2B.

To demonstrate this offline normalization procedure, the following experiment was performed in which a 3×3 NTR1 membrane protein array 210 was illuminated by a laser beam 204 emitted from a 355 nm laser 202. Then, the native fluorescence image of the protein array 210 in a 5 mm×5 mm field of view was taken by a CCD camera 214 (see the fluorescence array imager 200 shown in FIG. 2B). The native fluorescence image of the 3×3 NTR1 membrane protein array 210 is shown in FIG. 3. Each sample spot in the 3×3 protein array contained the same amount of NTR1 protein membrane samples (which were loaded onto a supporting substrate by a commercial liquid delivery system). As such, the sample spots in the 3×3 NTR1 membrane protein array 216 should all have the same intensity level of emitted fluorescence 205b within the native fluorescence image. However, the native fluorescence image shows uneven fluorescence intensities with respect to the sample's spots. This happened because the excitation laser beam 204 had a non-uniform intensity distribution.

Figure 4:
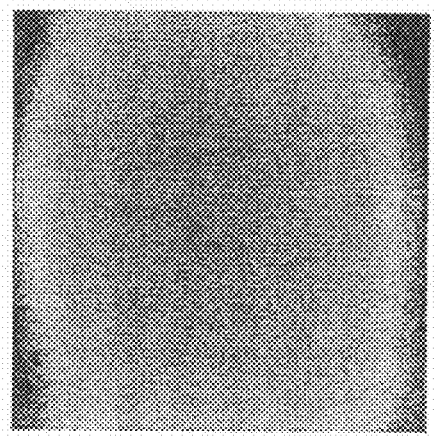
FIG. 4 is a fluorescence image of an Eu-doped glass that was excited by a 355 nm laser which was associated with a fluorescence array imager that was set-up like the one shown in FIG. 2A.

Next, a 2D fluorescence image of a glass 201 homogeneously doped with $Eu^{3+}$ (rare earth ion) was taken by a CCD camera 214 (see the fluorescence array imager 200 shown in FIG. 2A). The reference 2D fluorescence image associated with the $Eu^{3+}$ doped glass 201 is shown in FIG. 4. Since, the glass 201 was homogeneously doped with Eu ions, the fluorescence intensity of each location in the 2D fluorescence image has a linear relationship to the power of the laser 202 at that location. As such, the 2D fluorescence image of the $Eu^{3+}$ doped glass 201 can be used as a reference/standard to normalize the native fluorescence image of the 3×3 NTR1 membrane protein array.

Figure 5:
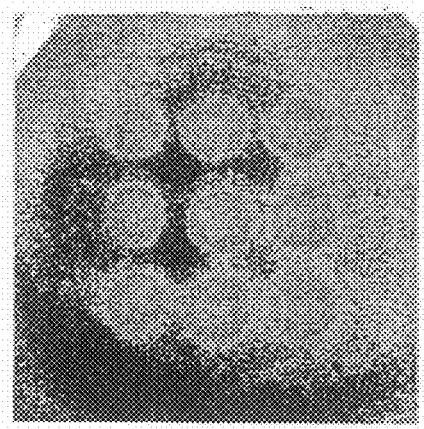
FIG. 5 is a normalized fluorescence image of the 3×3 NTR1 membrane protein array that was created by using the offline normalization fluorescence image process in accordance with the one of the embodiments of the present invention.
Figure 6:
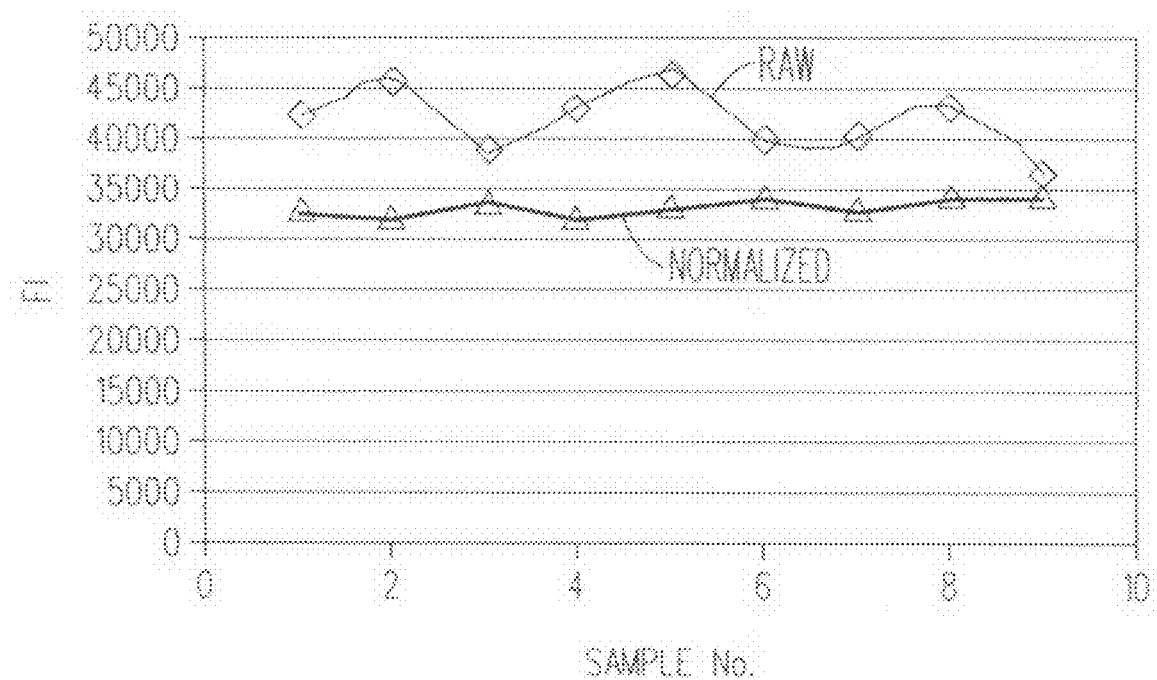
FIG. 6 is a graph that quantitatively illustrates the difference between the two fluorescent images of the 3×3 NTR1 membrane protein array which are shown in FIGS. 3 and 5.
Figure 7:
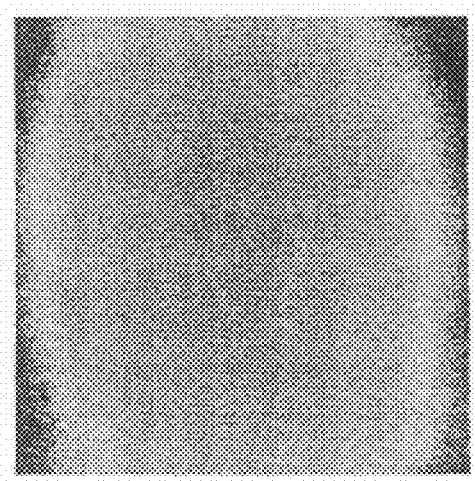
FIG. 7 is a fluorescence image of a Sm-doped glass that was excited by a 355 nm laser which was associated with a fluorescence array imager that was set-up like the one shown in FIG. 2A.

Finally, the native fluorescence image of the 3×3 NTR1 membrane protein array was normalized by dividing it into the fluorescence image of the $Eu^{3+}$ doped glass 201 (see equation no. 3). The normalized fluorescence image of the 3×3 NTR1 membrane protein array is shown in FIG. 5. As can be seen, the 9 sample spots in the normalized fluorescence image have similar fluorescence intensities. A quantitative comparison of the fluorescence intensity of the 3×3 NTR1 membrane protein array before and after the offline normalization is provided in FIG. 6. As can be seen, there was a significant improvement with the signal uniformity after the offline normalization process was performed. In yet another experiment, a $Sm^{3+}$ doped glass 201 was tested and deemed to be effective at correcting the native fluorescence image of the 3×3 NTR1 membrane protein array. The fluorescence image of the tested $Sm^{3+}$ doped glass 201 is shown in FIG. 7 (compare to FIG. 4).

Figure 8:
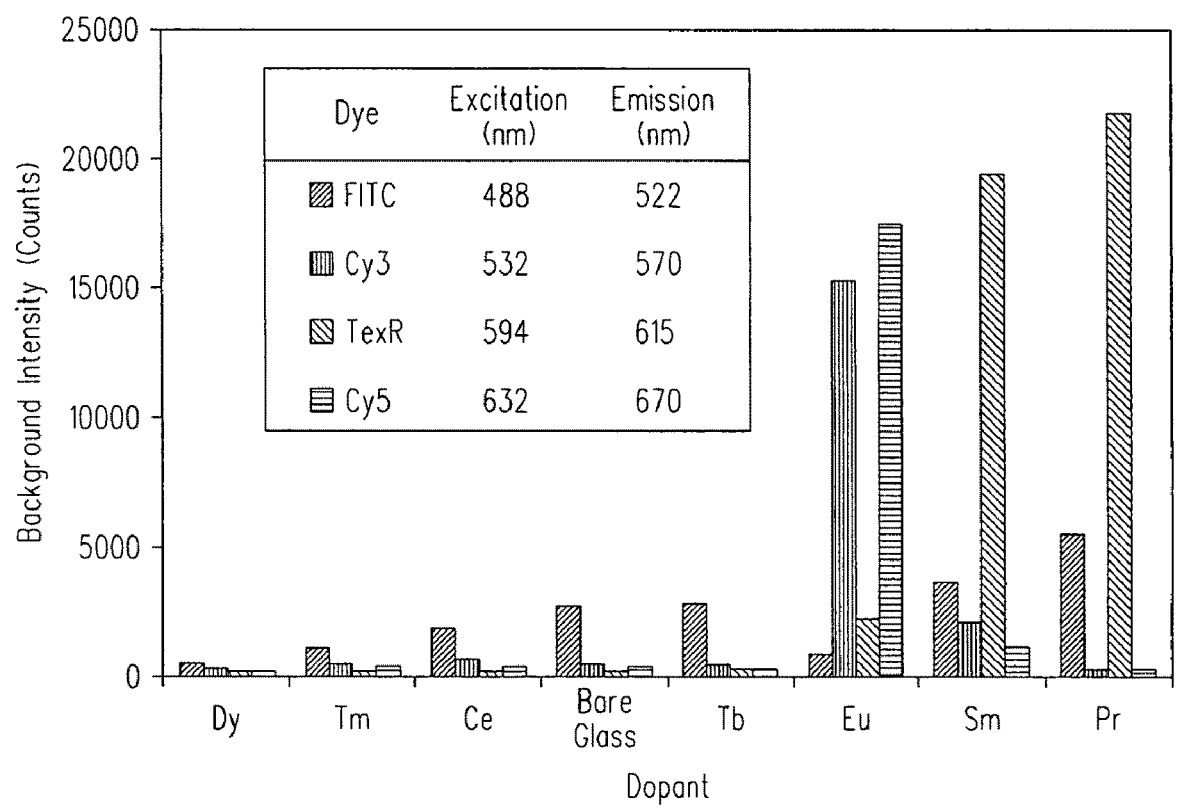
FIG. 8 is a graph that indicates the background (emitted) fluorescence of glass doped with a rare earth ion like $Eu^{3+}$, $Sm^{3+}$, $Pr^{3+}$, $Sb^{3+}$ relative to a bare microscopic slide.

A detailed discussion is provided next about how the glass 201 can be doped with a specific fluorescent ion so it can function as a reference/standard to normalize fluorescence images of test samples that contain a specific type of dye. FIG. 8 is a graph that indicates a background fluorescence of glass 201 doped with a rare earth ion like $Eu^{3+}$, $Sm^{3+}$, $Pr^{3+}$, $Sb^{3+}$ relative to a bare microscope slide. This graph indicates that $Eu^{3+}$, $Sm^{3+}$ and $Pr^{3+}$ have significant overlap with the fluorescent dyes and are suitable dopants which can help correct fluorescent images of test samples which contain Cy3, Cy5, and Texas Red dyes (note: in the offline normalization process it is desirable if the doped glass 201 and test sample(s) both absorb illuminated light at a first wavelength and both emit fluorescence at a second wavelength).

Figure 9:
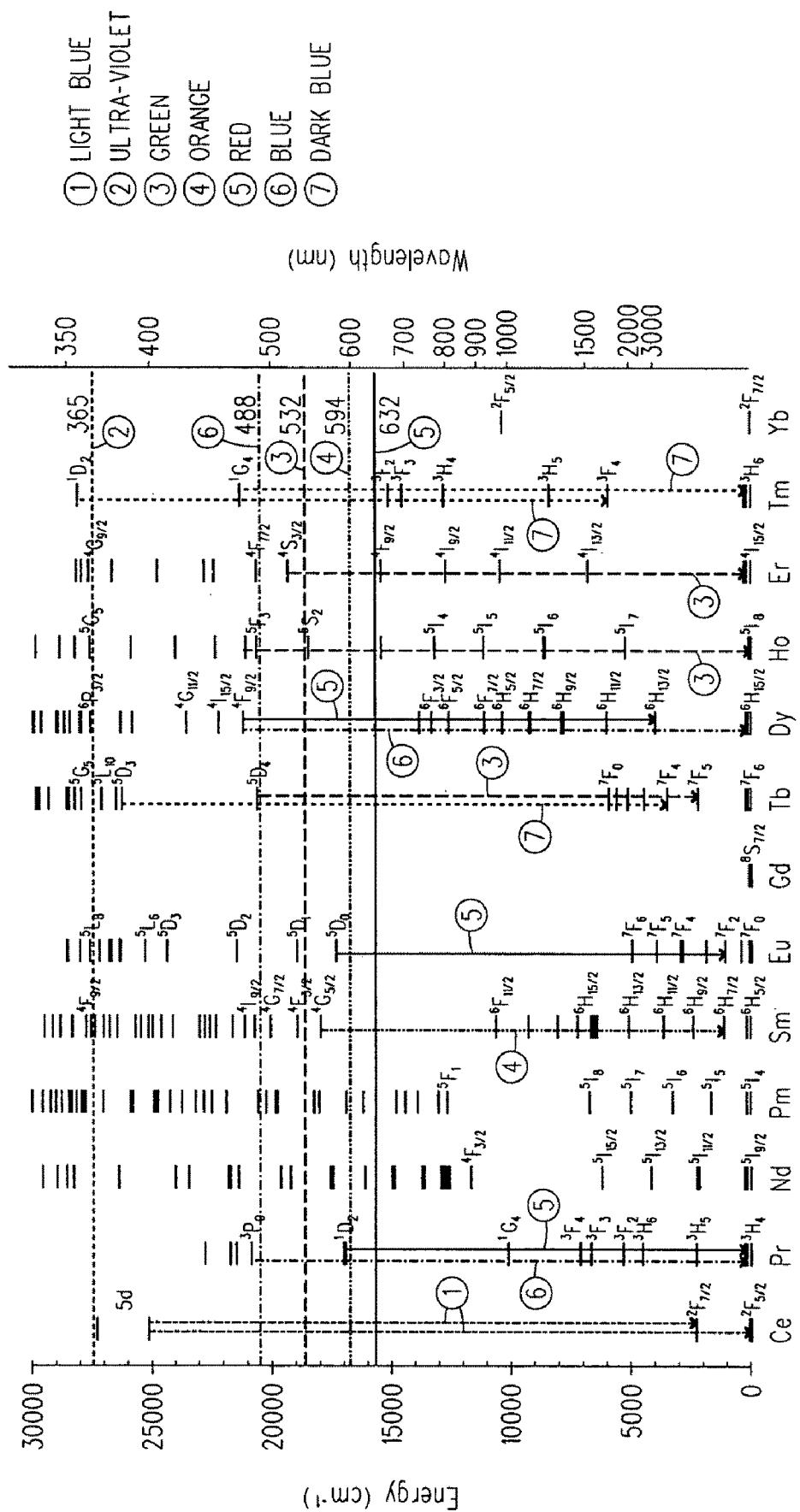
FIG. 9 is an energy level diagram of rare earth ions overlaid with common laser excitation sources with vertical lines showing some transitions that result in visible fluorescence.

In the event, the test sample contains a blue emitting dye such as FITC (fluorescein isothiocyanate), then the fluorescent image could be corrected (normalized) by shifting the emission wavelength which is monitored by the imaging device 214. To accomplish this, an emission filter 218 (or monochrometer 218) is placed in front of the imaging device 214 which shifts the wavelength that the fluorescent images of the test sample and the doped glass 201 are taken by the imaging device 214. The shifting of the monitoring emission wavelength works well as can be seen in the graph of FIG. 9. This graph shows that the energy levels of $Pr^{3+}$ and $Tb^{3+}$ overlap with the 488 nm FITC excitation (FITC is a blue dye). And, it shows that the emissions of $Pr^{3+}$ and $Tb^{3+}$ are in the red and green portion of the visible spectrum, respectively. As such, the use of an emission filter 218 (or monochrometer 218) which passes this red or green emission would better enable $Pr^{3+}$ and $Tb^{3+}$ doped glass 201 to correct the native fluorescent images (where the test samples 210 contain FITC dye).

Figure 10:
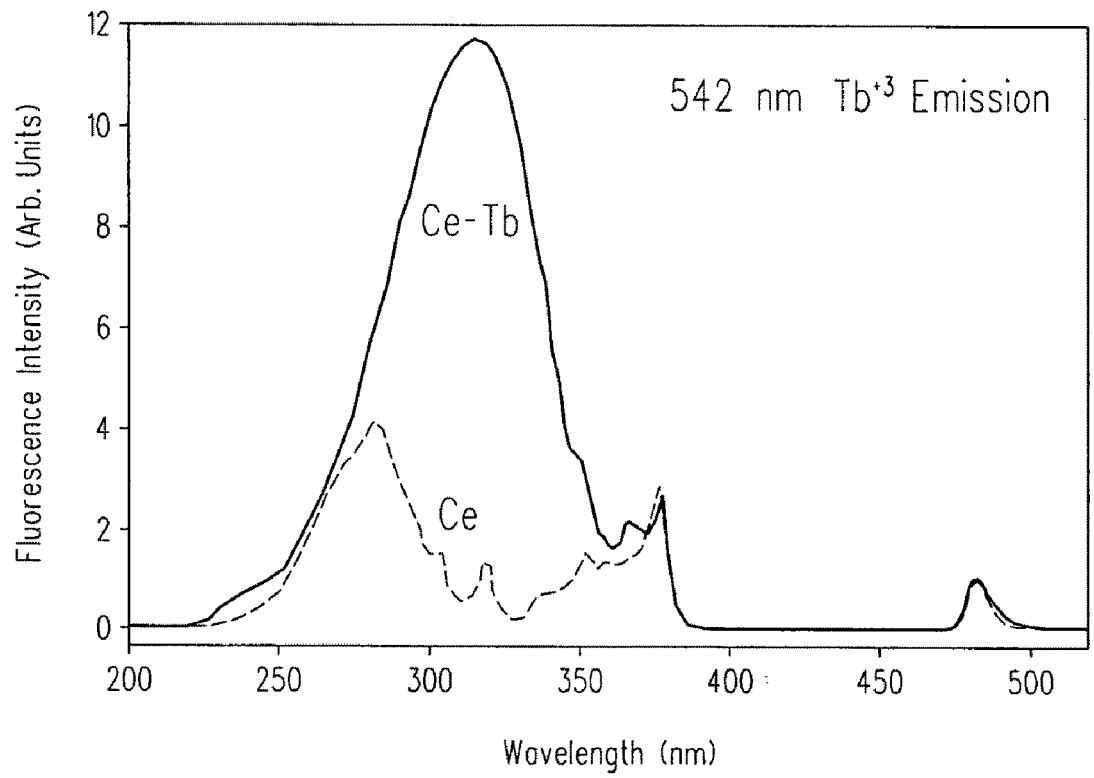
FIG. 10 is a graph (excitation spectra of 542 nm $Tb^{3+}$ emission) that shows the difference in the excitation spectra between a glass doped only with $Tb^{3+}$ versus a glass that is doped with $Tb^{3+}$ and also contains a Ce sensitizing co-dopant.
Figure 11:
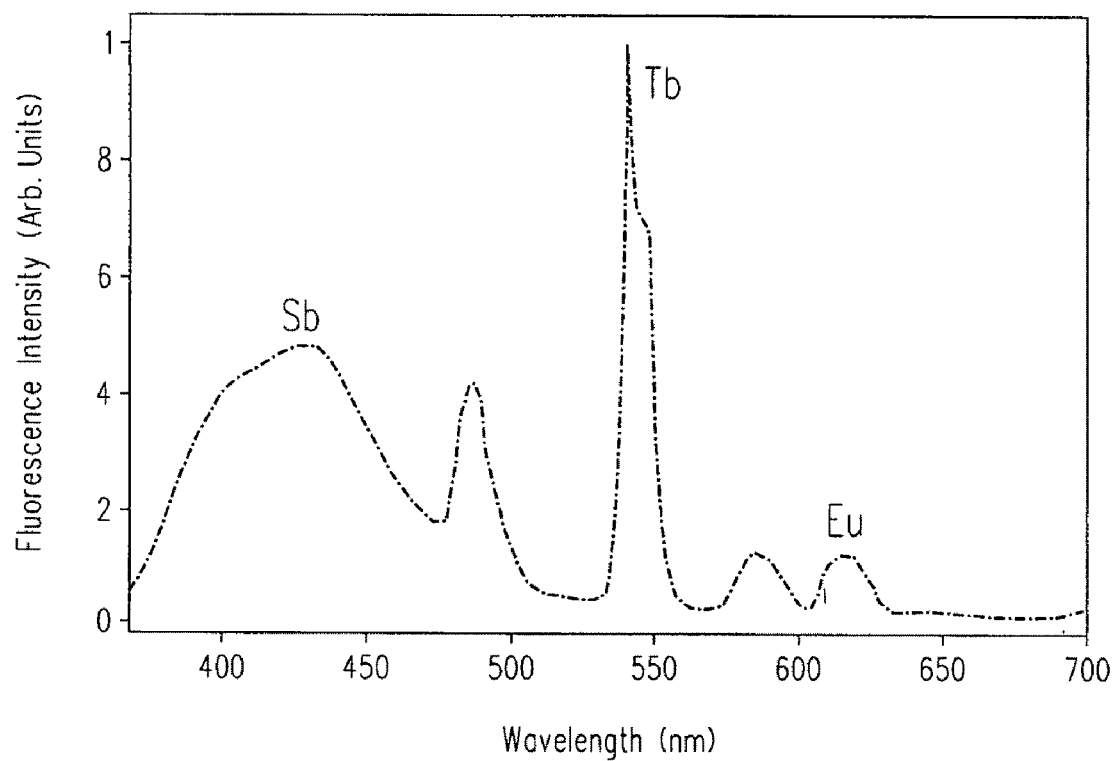
FIG. 11 is a graph that shows the emission spectra of a glass doped with $Sb^{3+}$, $Tb^{3+}$ and $Eu^{3+}$.

Referring now to FIGS. 10 and 11, it can be seen how the use of co-dopants within the doped glass 201 can change the excitation spectra and the emission spectra, respectively. In FIG. 10, there is a graph that shows the difference in the excitation spectra between a glass 201 doped only with $Tb^{3+}$ versus a glass 201 that is doped with $Tb^{3+}$ and also had Ce as a sensitizing co-dopant. The sensitizing co-dopant Ce was used to absorb light which is not absorbed by the emitting dopant $Tb^{3+}$, and then transfer this absorbed energy to the emitting dopant $Tb^{3+}$ thereby enhancing the amount of emitted light. In this example, the Ce sensitizing co-dopant was added to absorb ultra violet light between 275 and 350 nm, and then transfer this absorbed energy to the 542 nm emitting ion $Tb^{3+}$. As can be seen, this type of co-doping would be useful in matching a dye or system that had an emission wavelength which overlapped with the $Tb^{3+}$ emission, but had a pump (light) of around 325 nm where $Tb^{3+}$ does not have a strong absorption. Of course, Ce is just one type of co-dopant and there are many different types of sensitizers which could be added to the doped glass 201 depending on the particular application (note: if desired co-dopants can be used to shift an emission wavelength of a doped glass 201).

Referring to FIG. 11, there is a graph that shows the white emission spectra of a $Sb^{3+}$, $Tb^{3+}$ and $Eu^{3+}$ doped glass 201. As can be seen, the $Sb^{3+}$ emits in the blue portion of the spectrum, $Tb^{3+}$ in the green portion of the spectrum, and $Eu^{3+}$ in the red portion of the spectrum, which together effectively cover the entire visible spectrum. As can be seen, this multiple doping enables the use of one doped glass 201 to normalize the fluorescence images of test samples that contain different types of dyes. If desired, the glass 201 could even be doped with UV and IR emitters like $Gd^{3+}$, and $Nd^{3+}$, $Yb^{3+}$, and $Er^{3+}$.

Figure 12:
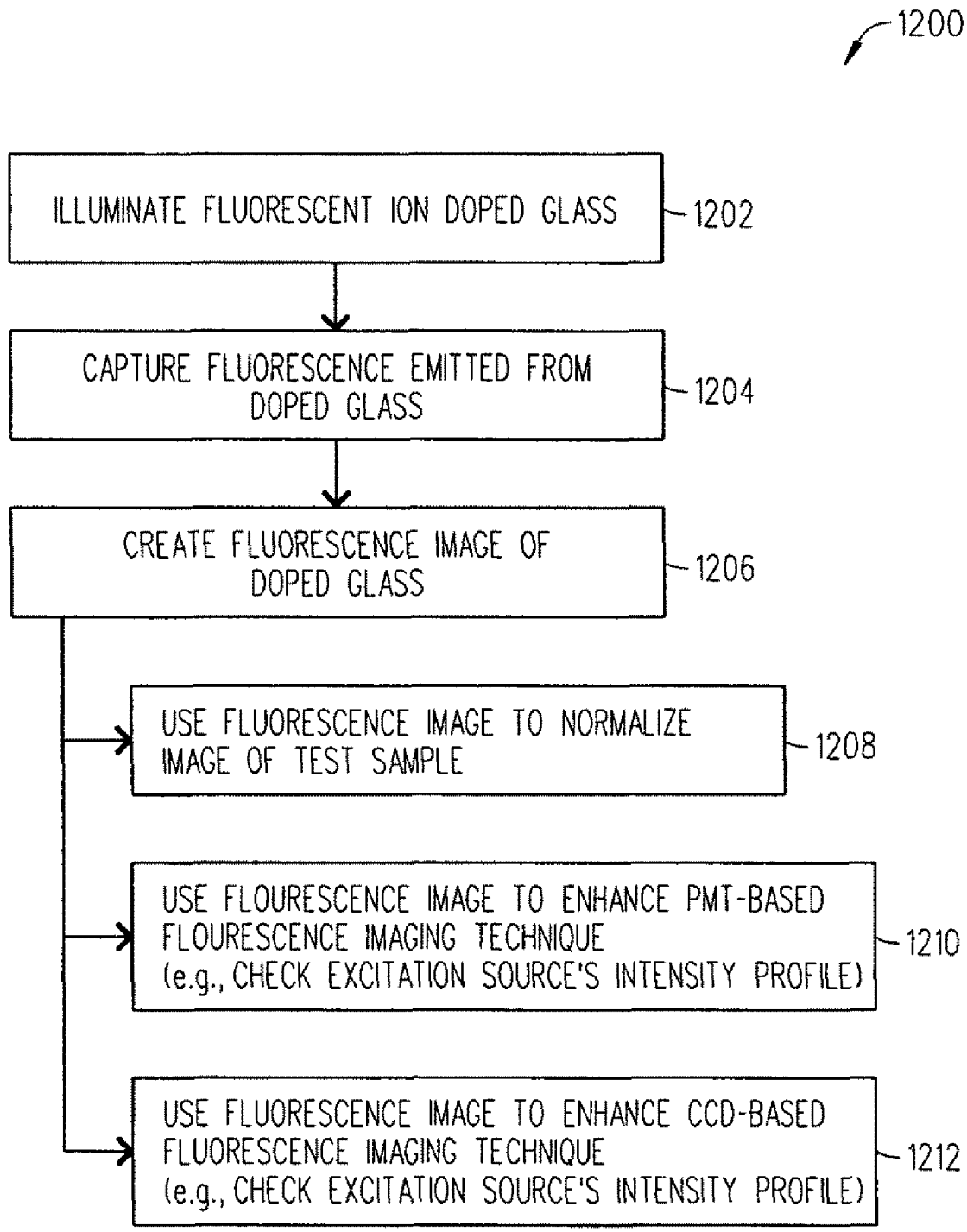
FIG. 12 is a flowchart that illustrates the basic steps of a preferred method for improving a fluorescence imaging technique in accordance with several different embodiments of the present invention.

Referring to FIG. 12, there is a flowchart illustrating the steps of a preferred method 1200 for improving a fluorescence imaging technique in accordance with several different embodiments of the present invention. Beginning at step 1202, the excitation source 202 (e.g., UV 355 nm laser 202) illuminates at least a portion of the fluorescent ion doped glass 201 (or other fluorescing material). At step 1204, the imaging device 214 (e.g., CCD camera 214) captures the fluorescence emitted 205a from the fluorescent ion doped glass 201. At step 1206, the imaging device (e.g., CCD camera 214) creates a fluorescence image based on the captured fluorescence 205a emitted from the fluorescent ion doped glass 201. Again, the fluorescence image of the fluorescent ion doped glass 201 is representative of a profile of the intensity distribution of the excitation source 202. As such, the fluorescence image of the fluorescent ion doped glass 201 can be used as a reference/standard to (for example): (1) normalize a fluorescence image of a test sample (e.g., protein array) (see step 1208) (this offline normalization of the fluorescence image of the test sample was discussed above with respect to FIGS. 2A-2B and 3-6); (2) check the uniformity of a laser light source which scans across the scanning area in a PMT based quantitative fluorescence imaging technique, and calibrate the fluorescence image if the intensity profile across the scanning region is repeatable (see step 1210); and (3) check the uniformity of a lamp light source in a CCD-based fluorescence imaging technique, and calibrate the fluorescence image if the light intensity pattern is repeatable (see step 1212).

Upto this point, an offline calibration approach has been discussed which can be used to compensate for the intensity non-uniformity associated with various excitation sources in quantitative fluorescence imaging techniques. In this offline calibration approach, a glass homogeneously doped with dopant(s) that fluoresce at a desired wavelength is imaged in a fluorescence imaging device. The resulting fluorescence image of the doped glass is used to normalize the fluorescence image of test samples generated from that same fluorescence imaging device such that the fluorescence intensity of the test sample image will be independent of the excitation source's intensity. However, this off-line calibration approach may not work very well under following circumstances: (1) when the intensity of the scanning beam fluctuates randomly during the scanning in a PMT-based scanning fluorescence imaging technique, or when the PMT-based scanner mechanical system instability impacts the beam intensity, then the illumination pattern in the scanning area is not repeatable over time which means that the offline normalization will not be able to compensate for the laser's intensity non-uniformity; (2) for CCD-based fluorescence non-scanning imaging techniques, if the intensity of the illumination source randomly fluctuates over time in a region of interest then this fluctuation will adversely affect the accuracy of the offline normalization approach. To address these concerns, an online illumination intensity calibration approach for quantitative fluorescence imaging techniques has been developed and is discussed next with respect to FIGS. 13-18.

In the online illumination intensity calibration approach, a piece of glass (or other material) homogeneously doped with fluorescing ions is used as the supporting substrate for the test samples (measurement target) such as a DNA array, protein array, etc. . . . . The homogeneously doped glass (or other material) and test samples (having a specific dye) are both made to absorb at the wavelength of the target excitation device (e.g., laser). But, the homogeneously doped glass (or other material) is made to emit fluorescence at a wavelength (reference channel) that can be differentiated from the emitted fluorescence wavelength (measurement channel) which is associated with the test sample. Thus, when the target sample (measurement target) is illuminated by the excitation source, properly designed optical filter combinations can be used to split the emitted fluorescence so two fluorescence images (or more if desired) can be generated: (1) the image of the target sample (measurement target) at the measurement channel; and (2) the image of the homogeneously doped glass (or other material) at the reference channel. Thereafter, the two images are compared with one another to normalize the fluorescence image of the target sample (this particular step is the same as was described above with respect to the offline calibration process and equation no. 3). Three exemplary fluorescence array imagers 1300, 1700 and 1800 are discussed next to help further explain this online illumination intensity calibration approach.

Figure 13:
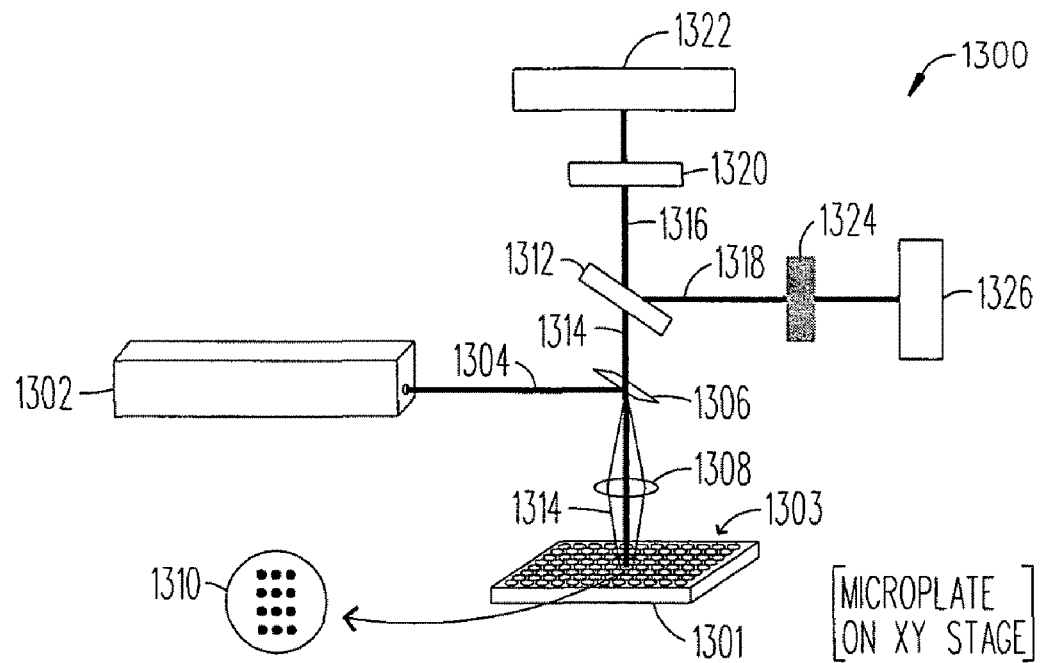
FIG. 13 is a block diagram illustrating an exemplary PMT-based scanning fluorescence array imager that is configured to interrogate a fluorescent ion doped glass on which there is placed target samples in accordance with an online calibration approach of the present invention.
Figure 14:
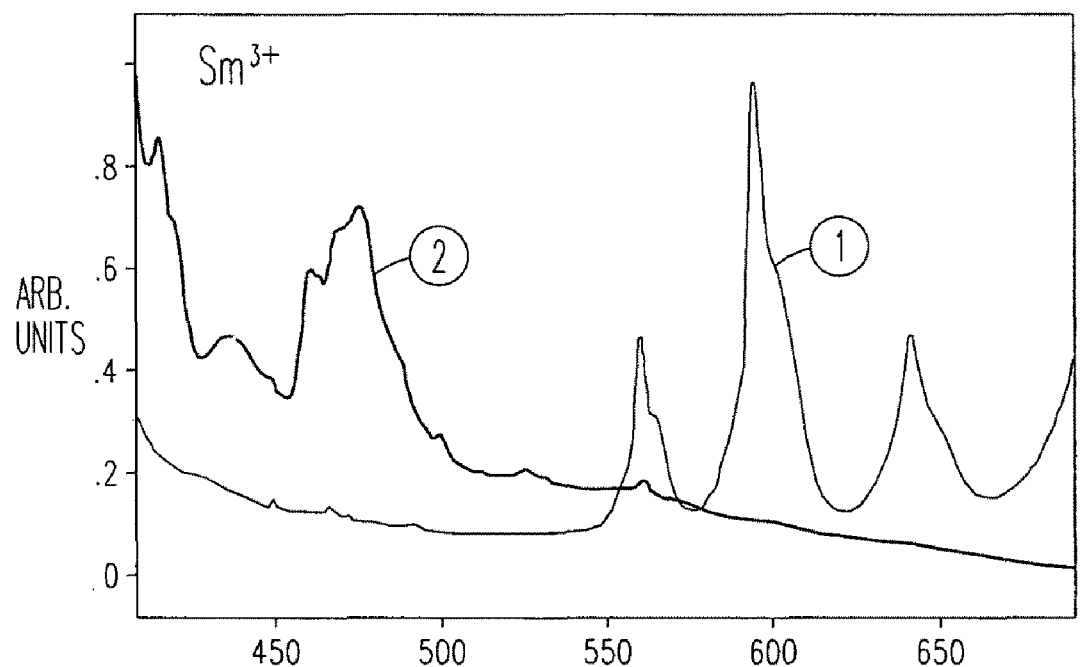
FIG. 14 is a graph that shows the absorption and emission spectra of a glass doped with $Sm^{3+}$.
Figure 15:
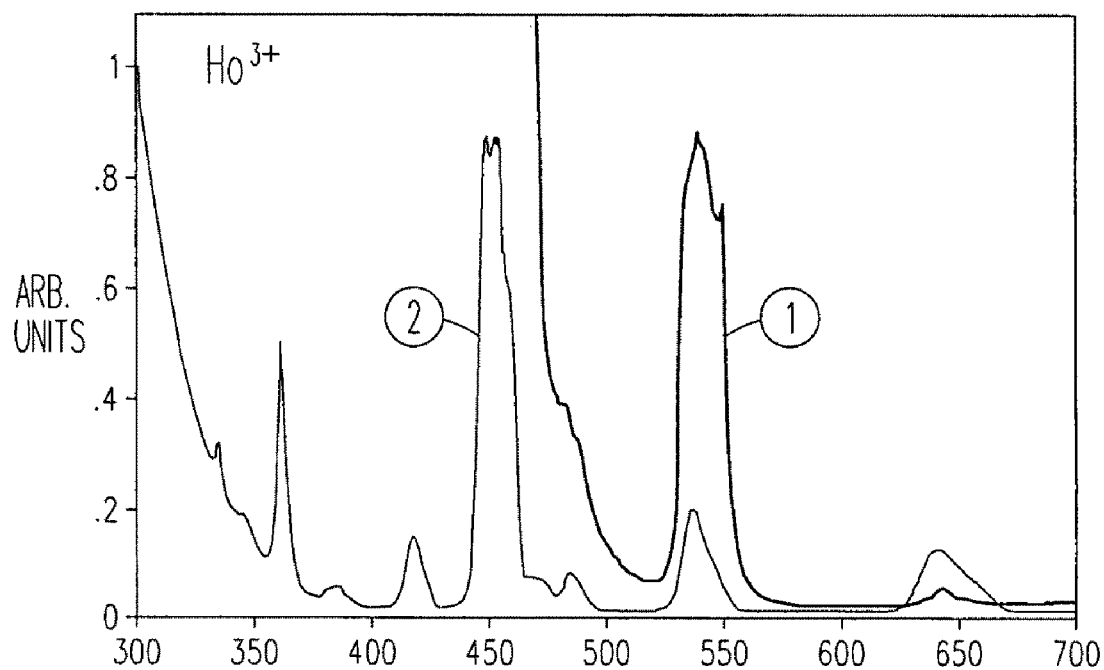
FIG. 15 is a graph that shows the absorption and emission spectra of a glass doped with $Ho^{3+}$.
Figure 16:
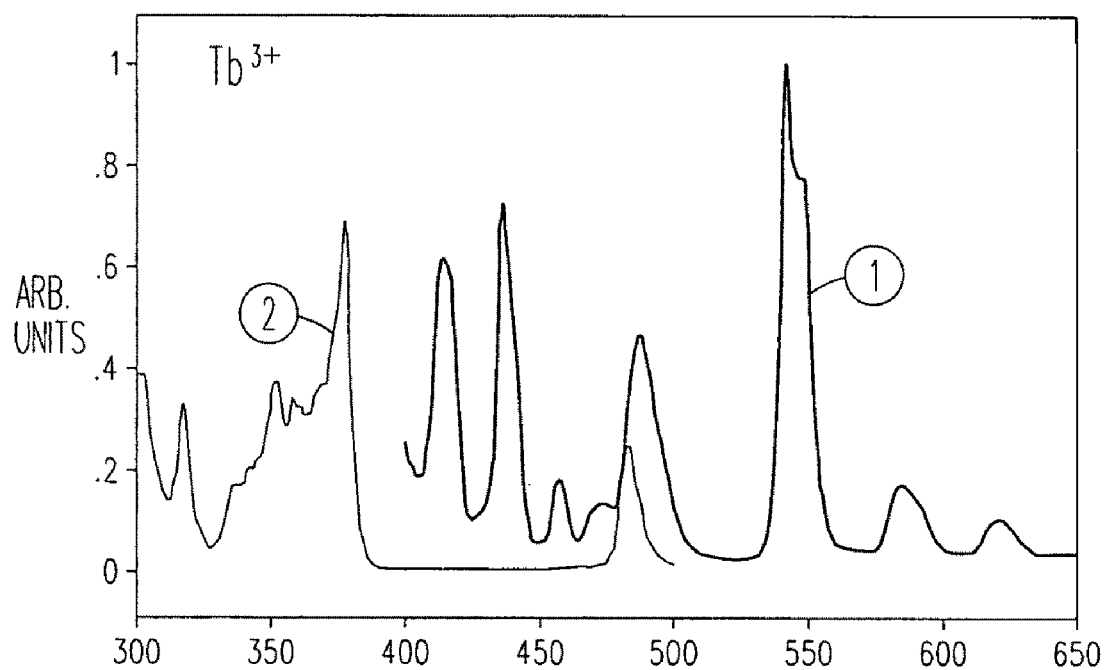
FIG. 16 is a graph that shows the absorption and emission spectra of a glass doped with $Tb^{3+}$.

Referring to FIG. 13, there is a block diagram illustrating an exemplary PMT-based scanning fluorescence array imager 1300 that is configured to interrogate the fluorescent ion doped glass 1301 on which there is placed target samples 1310 in accordance with the online calibration approach of the present invention. The exemplary fluorescence array imager 1300 shown includes an excitation source 1302 (e.g., laser 1302) which emits an optical beam 1304 that is reflected by a dichroic mirror 1306 and passed through a lens 1308 before it illuminates a portion of the fluorescent ion doped glass 1301 on which there is placed the target sample(s) 1310. In this example, the fluorescent ion doped glass 1301 is the bottom portion of a microplate 1303 that has wells in which there is placed the test sample(s) 1310. The fluorescent ion doped glass 1301 and target samples 1310 are both made to absorb light at the wavelength of the excitation source 1302. But, the fluorescent ion doped glass 1301 is made to emit fluorescence at a first wavelength (reference channel) and the target sample(s) 1310 is made to emit fluorescence at a second wavelength (measurement channel). For example, to use this approach to achieve real time illumination intensity calibration for a Cy3 measurement channel (where the target samples 1310 contain the Cy3 dye), the dopant in the supporting homogeneously doped glass 1301 (or other material) should absorb at 535 nm, and emit at a wavelength that does not overlap with the emission band of Cy3 at 570 nm. Both $Ho^{3+}$ and $Sm^{3+}$ doped glasses 1301 absorb at 535 nm but have little or no emission at 570 nm (see FIGS. 14 and 15 wherein the numeral "2" indicates absorption and the numeral "1" indicates emission).

Of course, there are other dopants (which are associated with the glass) that can be used to calibrate other dyes (which are associated with target samples 1310). For example, the dye FITC is typically excited at 488 nm and $Ho^{3+}$ and $Tb^{3+}$ both have absorptions at 488 nm and no fluorescence at 522 nm where FITC is typically detected (see FIGS. 15 and 16 wherein the numeral "2" indicates absorption and the numeral "1" indicates emission). Thus, $Ho^{3+}$ and $Tb^{3+}$ dopants can be used to calibrate systems where the target samples 1310 use a FITC dye. In addition, $Ho^{3+}$ has absorption near 632 nm which overlaps with that of the Cy5 dye, but no emission at 670 nm where Cy5 is detected. If desired, optimal system performance could be obtained by slightly shifting the detection wavelengths. For example, it was noted that while $Ho^{3+}$ has no emission at 670 nm, its fluorescence is quite strong at slightly shorter wavelengths, so it would be advantageous to collect the Cy5 signals at longer wavelengths like 680 nm where the Cy5 signal is strong but further from the interfering with $Ho^{3+}$ signal. To accomplish this, combinations of fluorescent ions and co-dopants can be used to increase the absorption at a desirable wavelength and/or shift the emission wavelength by transferring energy. In addition, the proper selection and combination of fluorescent ions and co-dopants in the glass substrate 1301 also enables the ability to interrogate multiple types of target sample(s) 1310 which contain different dyes.

Referring back to FIG. 13, the fluorescence array imager 1300 includes a beam splitter 1312 which is used to split the fluorescence emission 1314 into two channels: (1) the measurement channel 1316 and (2) the reference channel 1318. In the measurement channel 1316, the emission signal from the target sample(s) 1310 is filtered with a measurement filter 1320 (which permits only fluorescence 1316 pass that is related to the emission of the target sample(s) 1310) and then is detected by a PMT detector 1322 (which generates a fluorescence image based on the fluorescence 1316 emitted from target sample(s) 1310) (note: other imaging devices can be used if desired such as a CMOS camera). In the reference channel 1318, the emission signal from the fluorescent ion doped glass 1301 is filtered with a reference filter 1324 (which permits only fluorescence 1318 pass that is related to the emission of the fluorescent ion doped glass 1301) and then is detected by a PMT detector 1326 (which generates a fluorescence image based on the fluorescence 1318 emitted from the fluorescent ion doped glass 1301) (note: other imaging devices can be used if desired such as a CMOS camera). The target sample's fluorescence image can be normalized by the doped glass fluorescence image by using the aforementioned equation no. 3. In this way, the normalized signal (normalized test sample fluorescence image) is a function of the concentration of the measurement target sample(s) 1310 and is independent of the illumination intensity of the excitation source 1302.

Figure 17:
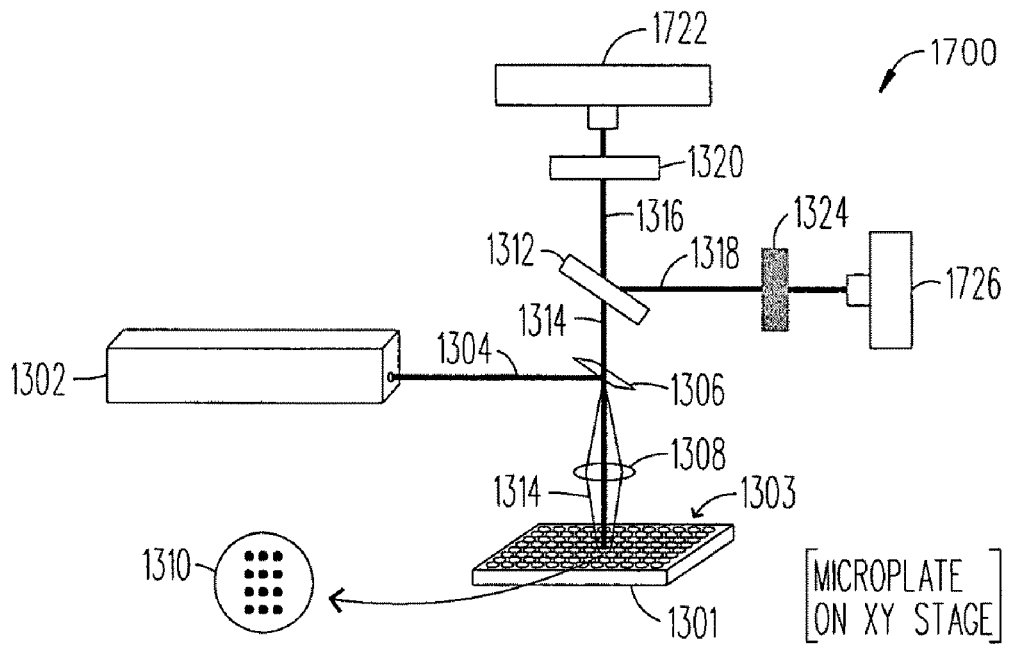
FIG. 17 is a block diagram illustrating an exemplary CCD-based fluorescence array imager (which has two CCD cameras) that is configured to interrogate a fluorescent ion doped glass on which there is placed target samples in accordance with the online calibration approach of the present invention.

Referring to FIG. 17, there is a block diagram illustrating an exemplary CCD-based fluorescence array imager 1700 that is configured to interrogate a fluorescent ion doped glass 1301 on which there is placed target samples 1310 in accordance with the online calibration approach of the present invention. The CCD-based fluorescence array imager 1700 has the same components as are used in the PMT-based scanning fluorescence array imager 1300 except that CCD detectors 1722 and 1726 are used instead of PMT detectors 1322 and 1326 (note 1: if desired a lamp 1302 could be used instead of the laser 1302 and in this case there would not be a need to scan the test samples 1310) (note 2: if desired other imaging devices can be used such as CMOS cameras). Since, the CCD-based fluorescence array imager 1700 (and the PMT-based scanning fluorescence array imager 1300) has a dual channel design then both the measurement fluorescence image and the reference fluorescence image are generated simultaneously which means the resulting normalized fluorescence image reflects the real-time intensity profile of the excitation source 1302 and is thus reliable.

Figure 18:
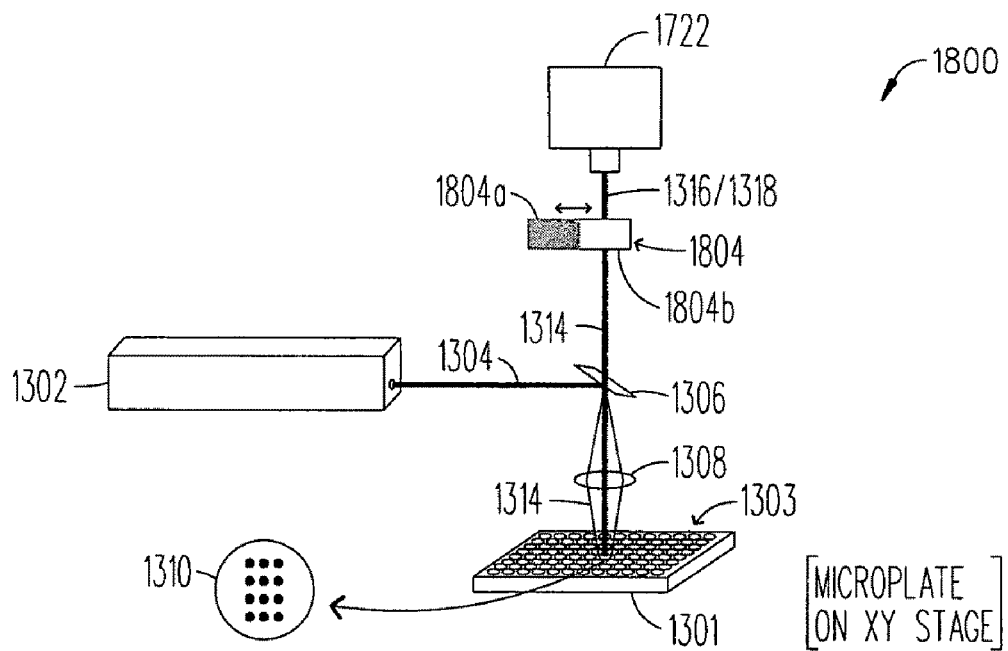
FIG. 18 is a block diagram illustrating an exemplary CCD-based fluorescence array imager (which has one CCD camera) that is configured to interrogate a fluorescent ion doped glass on which there is placed target samples in accordance with the online calibration approach of the present invention.

Referring to FIG. 18, there is a block diagram illustrating another exemplary CCD-based fluorescence array imager 1800 that is configured to interrogate a fluorescent ion doped glass 1301 on which there is placed target samples 1310 in accordance with the online calibration approach of the present invention. The CCD-based fluorescence array imager 1800 has the same components as are used in the CCD-based fluorescence array imager 1700 except that there is only one CCD detector 1802 and a modulating reference filter/measurement filter 1804 is used instead of the stationary reference filter 1324 and the stationary measurement filter 1320. In this application, the CCD detector 1802 sequentially captures images of the doped glass 1301 and the test sample(s) 1310 by modulating the combined reference filter/measurement filter 1804 (which includes a reference filter 1804*a* and a measurement filter 1804*b*). Because, the intensity spatial profile of the excitation beam 1304 is normally fairly stable over a reasonable period, for example, hours, an online approach that is not a real-time calibration approach like this may be used and it would also be very attractive in terms of cost (i.e., only one CCD camera is needed). In conclusion, the online calibration capability of fluorescence array imagers 1300, 1700 and 1800 provides reliable source intensity calibration when the excitation source intensity profile is not stable over time, or the excitation intensity pattern in the region of the interest is non-repeatable due to an unstable output of the excitation source or if there is a random mechanical fluctuation.

Although a fluorescent ion doped glass was described herein it should be appreciated that different types of uniformly fluorescing materials can be utilized instead. Exemplary uniformly fluorescing materials include a single crystal, a ceramic, a polymer, a paint, a phosphor coating etc. . . . . However, the fluorescent ion doped glass 202 is preferable due to its low scatter, good durability, and low cost.

Following is a list of some additional advantages, features and uses of the present invention:

(1) Simplicity. No additional optics, hardware and system redesign is needed to normalize the intensity of the excitation source.

(2) The post-normalization of excitation intensity does not sacrifice the power of the excitation source.

(3) The normalization process corrects the non-uniformities of the excitation source in addition to correcting the non-uniformities of the collection optics and the imaging device(s). This procedure works even as the illuminations source, collection optics and imaging device(s) age or accumulate dust and dirt.

(4) The doped glass can be made with ppm level homogeneity.

(5) The doped glass is not only stable over time but it is also optically stable, does not bleach, and has a good efficiency.

(6) The doped glass can be engineered to absorb and emit at different wavelengths.

(7) The doped glass has a long lifetime which permits time gating to eliminate background fluorescence and noise.

(8) The doped glass can be co-doped with other fluorescent ions to increase absorption at wavelengths where single dopants do not absorb or do not absorb well (see FIG. 11).

(9) The doped glass can be co-doped with other fluorescent ions to upconvert IR (infrared) wavelengths to visible wavelengths where detection is much easier.

(10) Lasers can now be used as excitation sources in the CCD-based fluorescence imaging techniques. The combination of laser and CCD camera is desirable for several reasons: (a) the different possible selections of a discrete wavelength laser offers more selective fluorescence signaling; (b) the high excitation energy level at the selected wavelength of the laser can improve detection sensitivity; and (c) the imaging based fluorescence life time study is possible now with short-pulsed (sub-nanosecond) laser sources.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. A method for obtaining an accurate fluorescence image of one or more test samples, said method comprising the steps of:
   illuminating at least a portion of a substantially uniform fluorescing material that is doped with a plurality of fluorescent ions or rare earth ions;
   capturing fluorescence emitted from the fluorescing material;
   creating a first fluorescence image based on the captured fluorescence emitted from the fluorescing material;
   illuminating the one or more test samples located on a non-fluorescing material, wherein the one or more test samples contain a fluorescent dye;
   capturing fluorescence emitted from the one or more test samples located on the non-fluorescing material;
   creating a second fluorescence image based on the captured fluorescence emitted from the one or more test samples on the non-fluorescing material; and
   comparing the first fluorescence image and the second fluorescence image to create a normalized fluorescence image of the one or more test samples which are located on the non-fluorescing material.

2. The method of claim 1, wherein said fluorescing material and said one or more test samples both absorb illuminated light at a first wavelength and both emit fluorescence at a second wavelength.

3. The method of claim 1, wherein said fluorescing material is:
   a glass;
   a single crystal;
   a ceramic;
   a polymer;
   a paint; or
   a phosphor coating.

4. The method of claim 1, wherein said fluorescing material has at least one of the following fluorescent ions: $Ce^{3+}$, $Ce^{4+}$, $Eu^{2+}$, $Eu^{3+}$, $Sm^{3+}$, $Pr^{3+}$, $Tb^{3+}$, $Dy^{3+}$, $Ho^{3+}$, $Tm^{3+}$, $Sn^{2+}$, $Mn^{n+}$, $As^{3+}$, $Sb^{3+}$, $Pb^{2+}$, $Cu^{+}$, $Bi^{n+}$, $Gd^{3+}$, $Nd^{3+}$, $Yb^{3+}$, $Er^{3+}$, an ultraviolet emittor and/or an infrared emittor.

5. The method of claim 1, wherein said one or more test samples contain a Cy3 dye, a Cy5 dye, a Texas Red dye and/or a FITC dye.

6. The method of claim 1, wherein the fluorescing material is doped with a co-dopant that absorbs light which is not absorbed by the fluorescent ions or the rare earth ions and transfers absorbed energy to the fluorescent ions or the rare earth ions thereby enhancing an amount of the fluorescence emitted from the fluorescing material.

7. The method of claim 1, wherein the one or more test samples include one or more protein arrays.

8. A method for obtaining an accurate fluorescence image of one or more test samples, said method comprising the steps of:
   illuminating at least a portion of a substantially uniform fluorescing material on which there is placed the one or more test samples, wherein the uniform fluorescing material is doped with a plurality of fluorescent ions or rare earth ions, and wherein the one or more test samples contain a fluorescent dye;
   capturing fluorescence emitted from the fluorescing material utilizing a reference filter, wherein the fluorescing material and the one or more test samples both absorb illuminated light at a first wavelength and the fluorescing material emits fluorescence at a second wavelength and the one or more test samples emit fluorescence at a third wavelength;
   capturing fluorescence emitted from the one or more test samples utilizing a measurement filter;
   creating a first fluorescence image based on the captured fluorescence emitted from the fluorescing material;
   creating a second fluorescence image based on the captured fluorescence emitted from the one or more test samples; and
   comparing the first fluorescence image and the second fluorescence image to create a normalized fluorescence image of the one or more test samples which are located on the fluorescing material.

9. The method of claim 8, wherein said fluorescing material is:
   a glass;
   a single crystal;
   a ceramic;
   a polymer;
   a paint; or
   a phosphor coating.

10. The method of claim 8, wherein said fluorescing material has at least one of the following fluorescent ions: $Ce^{3+}$, $Ce^{4+}$, $Eu^{2+}$, $Eu^{3+}$, $Sm^{3+}$, $Pr^{3+}$, $Tb^{3+}$, $Dy^{3+}$, $Ho^{3+}$, $Tm^{3+}$, $Sn^{2+}$, $Mn^{n+}$, $As^{3+}$, $Sb^{3+}$, $Pb^{2+}$, $Cu^{+}$, $Bi^{n+}$, $Gd^{3+}$, $Nd^{3+}$, $Yb^{3+}$, $Er^{3+}$, an ultraviolet emittor and/or an infrared emittor.

11. The method of claim 8, wherein said one or more test samples contain a Cy3 dye, a Cy5 dye, a Texas Red dye and/or a FITC dye.

12. The method of claim 8, wherein the fluorescing material is doped with a co-dopant that absorbs light which is not absorbed by the fluorescent ions or the rare earth ions and transfers absorbed energy to the fluorescent ions or the rare earth ions thereby enhancing an amount of the fluorescence emitted from the fluorescing material.

13. The method of claim 8, wherein the one or more test samples include one or more protein arrays.

* * * * *